(12) United States Patent
Brezeanu et al.

(10) Patent No.: US 9,349,801 B2
(45) Date of Patent: May 24, 2016

(54) METHOD AND SYSTEM FOR DIAMOND-BASED OXYGEN SENSOR

(71) Applicant: Honeywell International Inc., Morris Plains, NJ (US)

(72) Inventors: Mihai Brezeanu, Bucharest (RO); Bogdan-Catalin Serban, Bucharest (RO); Viorel Georgel Dumitru, Prahova (RO); Octavian Buiu, Bucharest (RO)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 14/828,718

(22) Filed: Aug. 18, 2015

(65) Prior Publication Data

US 2016/0056239 A1 Feb. 25, 2016

(30) Foreign Application Priority Data

Aug. 25, 2014 (EP) .................................... 14182173

(51) Int. Cl.
*H01L 29/16* (2006.01)
*G01N 27/414* (2006.01)
*H01L 29/45* (2006.01)

(52) U.S. Cl.
CPC ........ *H01L 29/1602* (2013.01); *G01N 27/4141* (2013.01); *H01L 29/45* (2013.01)

(58) Field of Classification Search
None
See application file for complete search history.

(56) References Cited

U.S. PATENT DOCUMENTS

| 5,362,975 A | 11/1994 | Von Windheim et al. |
| 2008/0203431 A1* | 8/2008 | Garcia ............... G01N 27/4141 257/192 |

FOREIGN PATENT DOCUMENTS

| EP | 2028483 A2 | 2/2009 |
| EP | 2889612 A1 | 7/2015 |

OTHER PUBLICATIONS

"European Application Serial No. 14182173.6 Response filed Jul. 7, 2015 to Extended European Search Report Response mailed Feb. 18, 2015", 33 pgs.
"European Application Serial No. 14182173.6, Extended European Search Report mailed Feb. 18, 2015", 8 pgs.
"Oxyfire Oxygen Sensor Installation/Operation Manual", © Marathon Monitors Inc. 2010, (2010), 19 pgs.
Brezeanu, M., "Diamond Schottky structures", *IEEE International Semiconductor Conference, CAS 2009*, (2009), 15-25.
Dubbe, A, "Fundamentals of solid state ionic micro gas sensors", *Sensors and Actuators B: Chemical,*. 88(2), (2003), 138-148.
Ramamoorthy, R., et al., "Oxygen sensors: Materials, methods, designs and applications", *J. of Mat. Sci.*, 38, (2003), 4271-4282.

(Continued)

*Primary Examiner* — Yasser A Abdelaziez
(74) *Attorney, Agent, or Firm* — Schwegman Lundberg & Woessner, P.A.

(57) ABSTRACT

A diamond based oxygen sensor is able to function in harsh environment conditions. The oxygen sensor includes a gateless field effect transistor including a synthetic, quasi-intrinsic, hydrogen-passivated, monocrystalline diamond layer exhibiting a 2-dimension hole gas effect. The oxygen sensor also includes a sensing layer comprising yttrium-stabilized zirconia deposited onto a surface of the gateless field effect transistor.

15 Claims, 2 Drawing Sheets

(56) References Cited

OTHER PUBLICATIONS

Yuji, Miyahara, "Characterization of sputtered yttriastabilized zirconia thin film and its application to a metalinsulatorsemiconductor structure", *Journal of Applied Physics*, 71(5), (Mar. 1992), 2309-2314.

Zhisheng, Zhang, et al., "A New Application of $ZrO_2$ Solid Electrolyte Thin-Film", *Transactions of Tianjin University*, 2(1), (May 1996), 86-88.

* cited by examiner

METHOD AND SYSTEM FOR DIAMOND-BASED OXYGEN SENSOR

BACKGROUND

Chemical sensors are widely used in industrial environments for process control, environmental control, and other applications. A chemical sensor is a device that monitors the concentration of a given chemical species in a liquid or a gas. Chemical sensors are often required to be highly sensitive in order to detect small concentrations of particular chemical species. They are also often required to withstand harsh chemical environments or high temperatures that may be present in process control, environmental control, or other applications. Various oxygen sensors have been used in ambient or in harsh environmental conditions, such as high radiation levels, high corrosion rates, high humidity levels, or in high temperatures.

There is an increased need for oxygen ($O_2$) sensors operating at high temperature and in adverse environments, such as highly corrosive environments or environments with high level of vibration. Increasingly, oxygen detectors are required in cars, aircrafts, and industrial applications to reduce emission and to monitor and optimize combustion. As oxygen sensors are often located adjacent to or within combustion engines, these oxygen sensors need to withstand ambient temperatures of at least 450° C. When mounted in furnaces, incinerators, or industrial boilers, in-situ oxygen detectors are required to cope with maximum operating temperatures ranging from 500° C. to 1600° C. Previous approaches for oxygen sensors included, amongst others, the use of semiconductors such as silicon or silicon carbide. However, the previous oxygen sensors require significant power consumption, and do not match the sensitivity level, response time, dimensions, and lifetime required for operation in harsh conditions.

SUMMARY

An oxygen sensor is based on a diamond field effect transistor using a gateless field effect transistor. The gateless field effect transistor includes a synthetic, quasi-intrinsic diamond layer exhibiting a 2-dimension hole gas effect. The quasi-intrinsic diamond layer is mono crystalline (e.g., single-crystal), and it is grown using chemical vapor deposition (CVD). The oxygen sensor includes a sensing layer based on yttrium-stabilized zirconia (YSZ) deposited onto a surface of the gateless field effect transistor.

DETAILED DESCRIPTION OF THE DRAWINGS

The embodiments of the present invention will be described, by way of example only, by reference to the accompanying drawings.

Figure 1:
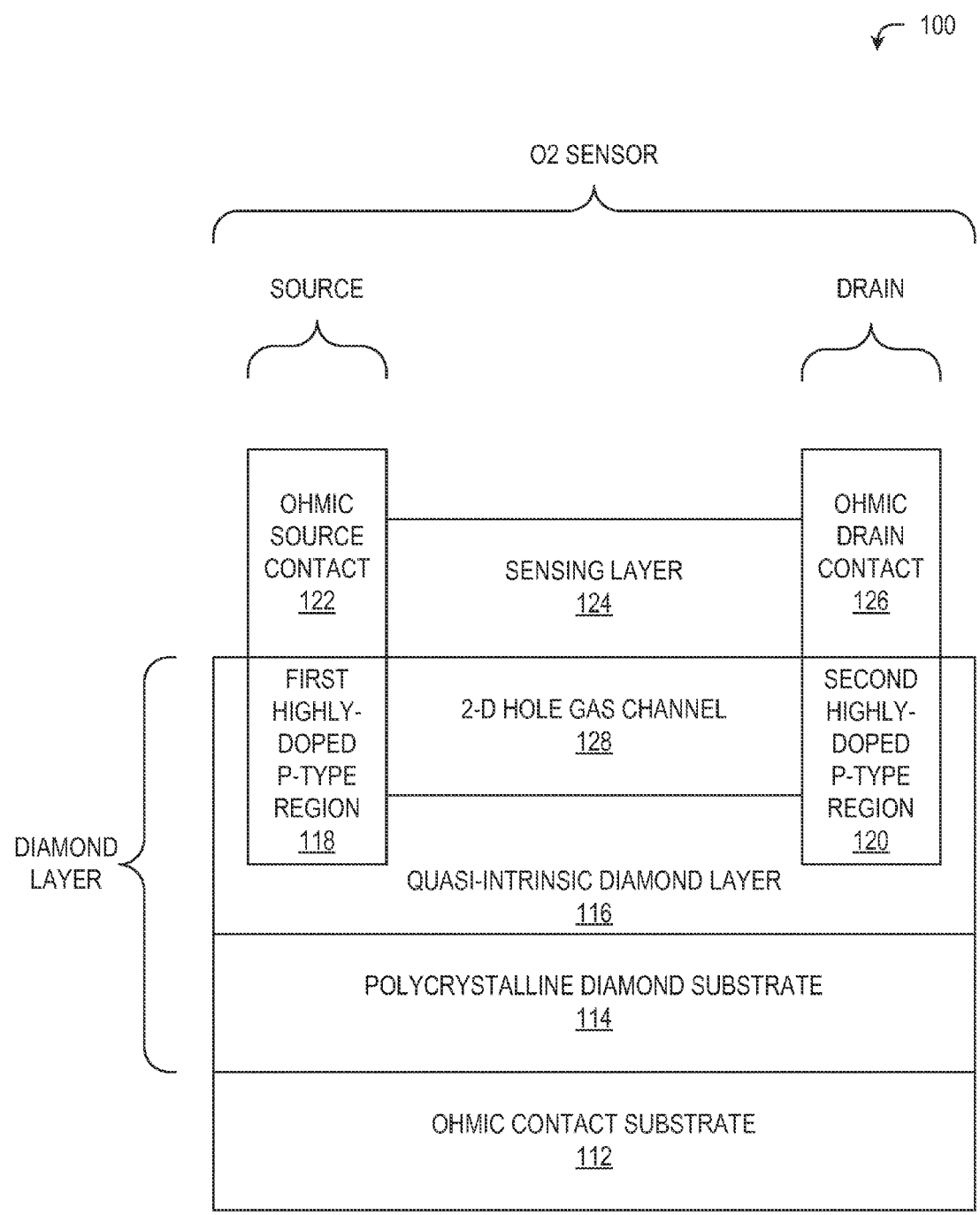
Figure 2:
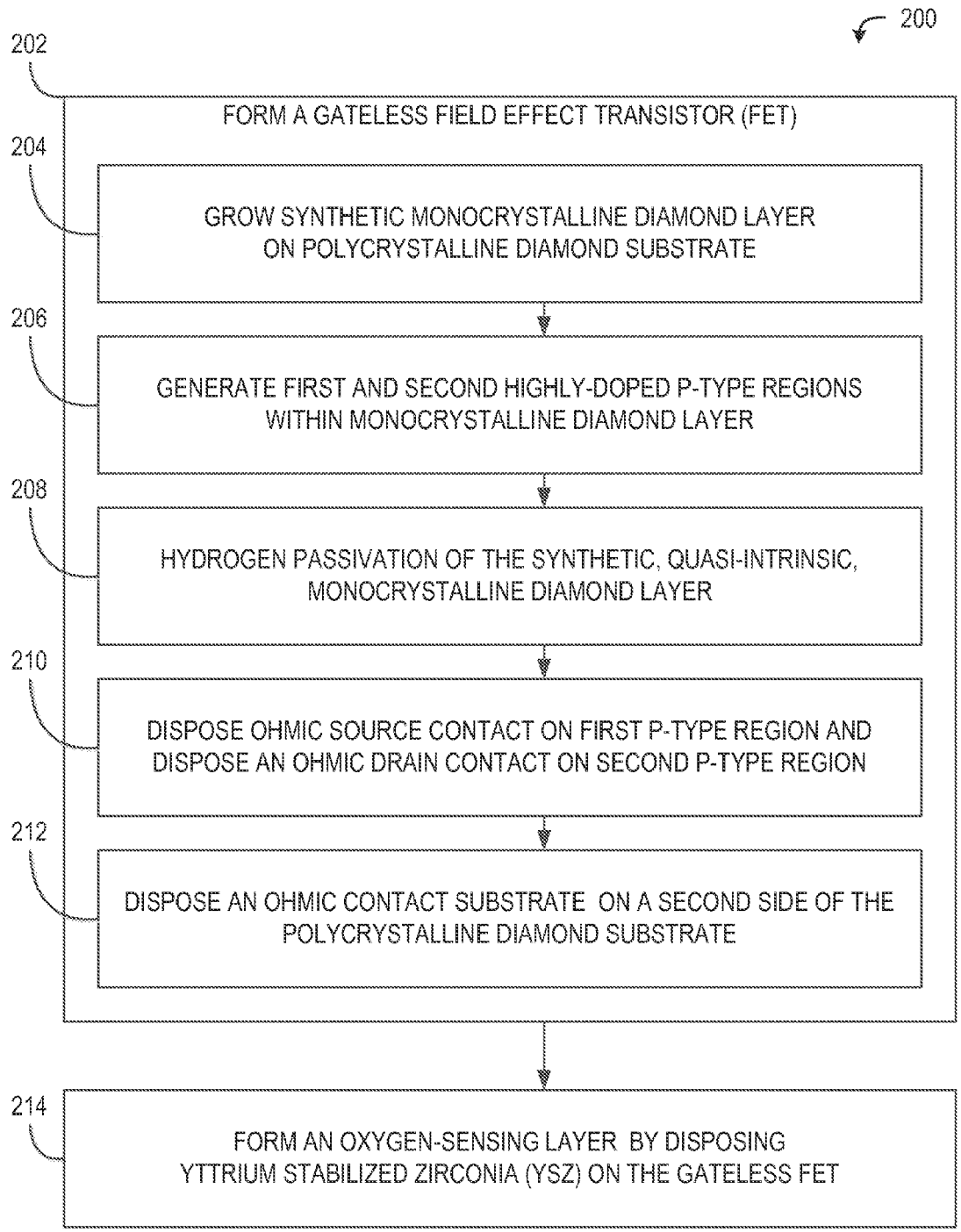

FIG. 1 shows a cross-sectional view of an oxygen sensor.
FIG. 2 shows a method of forming an oxygen sensor.

DETAILED DESCRIPTION

Examples of the present disclosure relate to an oxygen sensor and method of making the oxygen sensor. Oxygen sensors may be used in applications such as combustions and emission monitoring in domestic and industrial boilers, in car and plane engines, the food industry, carbon storage and sequestration, oil and gas storage and transportation. These applications generally require oxygen sensors with increased sensitivity levels, lower response time, reduced power consumption, and longer lifetime. The oxygen sensors of the present disclosure may have a high oxygen sensitivity, low power consumption and limited cross-sensitivity. The oxygen sensors may be manufactured using synthetic diamond, and may be used in harsh conditions.

In some examples, the oxygen sensor may include a gateless field effect transistor including a synthetic, quasi-intrinsic, monocrystalline diamond layer exhibiting a 2-dimension hole gas effect. The oxygen sensor may include a sensing layer. The sensing layer may include yttrium-stabilized zirconia (YSZ) deposited onto a surface of the gateless field effect transistor.

In some examples, the oxygen sensor may include a synthetic diamond substrate, which may be either monocrystalline or polycrystalline, and an ohmic contact coupled to the substrate. In an example, a synthetic, quasi-intrinsic, monocrystalline diamond layer may be grown and hydrogen-passivated on the synthetic diamond substrate forming a synthetic, quasi-intrinsic, hydrogen-passivated, monocrystalline, diamond layer (e.g., quasi-intrinsic diamond layer). The quasi-intrinsic diamond layer may be grown by chemical vapor deposition (CVD). A 2-dimensional (2D) conductive channel may form along the surface of the quasi-intrinsic diamond layer. The 2D conductive channel may consist of holes (2D hole gas (2DHG) effect), a phenomenon which refers to the presence of a gas of holes, free to move in two dimensions only. This effect naturally occurs at the surface of the synthetic, quasi-intrinsic, hydrogen-passivated diamond layer. The sensing layer may be adjacent to the 2D conductive channel. That is, the sensing layer is deposited onto a surface of the gateless field effect transistor that is above the 2D conductive channel.

Two highly-doped p-type regions may be created within the quasi-intrinsic diamond layer. For example, the p-type regions may be created by ion implantation (e.g., with boron atoms) and a maximum doping concentration, for example, may be about $10^{20}$ $cm^{-3}$. The oxygen sensor may further include an ohmic substrate contact, an ohmic source contact, and an ohmic drain contact. The ohmic source contact and the ohmic drain contact may be positioned on each of the two highly-doped p-type regions. The yttrium-stabilized zirconia (YSZ) sensing layer may be deposited onto the surface of the quasi-intrinsic diamond layer between two ohmic contacts, such as between an ohmic source contact and an ohmic drain contact.

The ohmic drain contact and the ohmic source contact may collect the current flowing through the 2D conductive channel. A current will flow through the 2D conductive channel from the source to the drain if there is a potential difference between the ohmic source contact and the ohmic drain contact. By avoiding the use of a gate, this configuration maximizes the area exposed to the oxygen. When changes occur in the oxygen concentration, the potential at the surface of the gateless field effect transistor changes, including below and along the sensing layer. This causes a variation in the 2D conductive channel carrier concentration, which results in a change of the drain-source current.

FIG. 1 shows a cross-sectional view of an oxygen sensor 100, in accordance with one example. The sensor 100 may include an ohmic substrate contact 112, a diamond substrate 114 (e.g., monocrystalline diamond substrate, polycrystalline diamond substrate), a synthetic, quasi-intrinsic, hydrogen-passivated, monocrystalline diamond layer 116 (e.g., quasi-intrinsic diamond layer), and a 2-dimensional hole gas channel 128. The quasi-intrinsic diamond layer 116 may include impurities in concentrations of less than $10^{13}$ $cm^{-3}$, and may be grown on the polycrystalline diamond substrate 114.

The ohmic substrate contact 112 may include metal stacks such as, but not limited to, titanium-aluminum, titanium-gold, titanium-platinum, and titanium-nickel. The sensor 100 may include omhic contacts such as an ohmic contact for the source 122 and an ohmic contact for the drain 126. The ohmic source contact 122 and the ohmic drain contact 126 may include metal stacks such as, but not limited to, titanium-aluminum, titanium-gold, titanium-platinum, and titanium-nickel. A current will flow from the source to the drain if there is a potential difference between the two contacts.

Sensor 100 may include two highly-doped p-type regions implanted within the quasi-intrinsic diamond layer 116. For example, sensor 100 may include a first highly-doped p-type region 118 and a second highly-doped p-type region 120. The first highly-doped p-type region 118 may be positioned below the ohmic source contact 122 and the second highly-doped p-type region 120 may be positioned below the ohmic drain contact 126. The highly-doped p-type regions 118 and 120 may be created by ion implantation (e.g., with boron atoms) and may have a maximum doping concentration of about $10^{20}$ cm$^{-3}$. The highly-doped p-type regions 118 and 120 may have a doping concentration between about $10^{19}$ cm$^{-3}$ to about $5\times10^{20}$ cm$^{-3}$, for example, about $5\times10^{19}$ cm$^{3}$ to about $2\times10^{20}$ cm$^{-3}$, such as $10^{20}$ cm$^{-3}$.

Between the drain and the source, on top of the quasi-intrinsic diamond layer, a YSZ layer is deposited. When introduced in a high temperature environment (e.g., at least 500° C.) and exposed to oxygen concentration changes in the ambient, the potential at the semiconductor surface in the FET structure changes, thus leading to large modifications of the channel carrier concentration. These large modifications of the channel carrier concentration then modify the drain-source current, where the current change is proportional to the oxygen concentration.

The chemical and physical properties of YSZ in an oxygen sensing structure enable the use of these oxygen sensors in adverse environments. Among the materials used as solid electrolytes in potentiometric oxygen sensors, YSZ may be used in harsh environment applications due to its remarkable hardness, chemical inertness, and because its composition and electrical properties are stable from room temperature up to 2500° C. The oxygen vacancies created when doping zirconia ($ZrO_2$) with yttria play a central role in the behavior of the sensor. The efficiency in capturing and releasing oxygen atoms is determined by the operating temperature. Although ionic conduction is triggered around 38° C., only at levels above 500° C. is the ionic conduction in YSZ strong enough to yield a significant current proportional to the oxygen concentration. Unlike other oxygen sensors, the combination of a single crystal synthetic diamond and YSZ only triggers oxygen sensing at high environmental temperatures experienced near or inside combustion environments, which advantageously does not require a heater. By avoiding the need for a heater, this oxygen sensor significantly reduces the power consumption.

In addition to the use of YSZ, this oxygen sensor takes advantage of several characteristics of single crystal synthetic diamond. Both YSZ and single crystal synthetic diamond materials are extremely hard and have excellent chemical and physical properties. Synthetic diamond has several properties that make it suitable for harsh environment applications, such as high thermal conductivity, increased hardness, fracture toughness, chemical inertness, high Young modulus, high melting and boiling points. When YSZ and single crystal synthetic diamond materials are coupled in an oxygen sensing structure, these materials have the potential to ensure the stability of the sensor in adverse environments conditions.

Another important property of synthetic diamonds occurs when a monocrystalline CVD diamond intrinsic layer is hydrogen-passivated, resulting in a 2DHG-like conductive channel appearing at the diamond surface. The concentration of holes is determined not by doping, but by the 2DHG effect. The oxygen sensor described herein takes advantage of the 2DHG effect occurring in hydrogen-passivated monocrystalline CVD diamond. The 2DHG effect refers to the presence of a gas of holes free to move in two dimensions only, but with very little freedom of movement in the third dimension. The 2DHG effect may occur at the surface of the synthetic, quasi-intrinsic, hydrogen-passivated, monocrystalline diamond layer and results in a tight confinement of holes leading to quantized energy levels for motion in the third dimension.

The 2-dimensional hole gas channel 128 may form along the surface of the quasi-intrinsic diamond layer 116. The YSZ sensing layer 124 may be deposited on the surface of the quasi-intrinsic diamond layer 116 that is adjacent to the 2-dimensional hole gas channel 128. When introduced in a high temperature environment (e.g., at least 500° C.) and exposed to oxygen concentration changes in the ambient, the potential at the semiconductor surface in the FET structure changes, thus leading to large modifications of the channel carrier concentration. This, in turn, modifies the drain-source current. The current change is proportional with the oxygen concentration, which enables current-based oxygen sensing.

FIG. 2 shows a method 200 of forming an oxygen sensor, in accordance with one example. The method 200 of forming an oxygen sensor may include at 202 forming a gateless field effect transistor (FET), such as the gateless FET shown in FIG. 1. Forming a gateless FET may include at 204 growing a synthetic, quasi-intrinsic, monocrystalline diamond layer on a first side of a polycrystalline diamond substrate. Growing the quasi-intrinsic diamond layer on top of the diamond substrate may be performed using CVD.

Forming a gateless FET may include at 206 using boron implantation to generate a first highly-doped p-type region and a second highly-doped p-type region within the diamond layer. At 208, the hydrogen passivation of the synthetic, quasi-intrinsic, monocrystalline diamond layer is performed. The hydrogen passivation is not performed over the 118 and 120 highly-doped p-type region. The hydrogen passivation leads to the generation of a 2-dimension hole gas conductive channel within the monocrystalline diamond layer between the first highly-doped p-type region and the second highly-doped p-type region. At 210, an ohmic source contact may be formed on the first highly-doped p-type region, and an ohmic drain contact may be formed on the second highly-doped p-type region. The ohmic source contact and the ohmic drain contact may be formed from a stack of Ti/Au. Forming a gateless FET may also include at 212 disposing an ohmic contact substrate on a second side of the polycrystalline diamond substrate. The method 200 of forming an oxygen sensor may include at 214 forming an oxygen-sensing layer by disposing YSZ on the gateless FET.

Example 1 includes an oxygen sensor comprising a gateless field effect transistor (FET) (100) including a synthetic, quasi-intrinsic, hydrogen-passivated diamond layer (116) exhibiting a 2-dimension hole gas effect, and an oxygen-sensing layer (124) including a yttrium-stabilized zirconia (YSZ) supported by the gateless FET (100).

Example 2 includes the oxygen sensor of example 1, the gateless FET (100) further including a first highly-doped p-type region (118) implanted within the monocrystalline diamond layer (116), a second highly-doped p-type region (120) implanted within the monocrystalline diamond layer (116), and a 2-dimension hole gas conductive channel (128)

at the surface of the monocrystalline diamond layer (116) between the first highly-doped p-type region (118) and the second highly-doped p-type region (120).

Example 3 includes the oxygen sensor of any of examples 1-2, the gateless FET (100) further including an ohmic source contact (122) electrically coupled to the first highly-doped p-type region (118), and an ohmic drain contact (126) electrically coupled to the second highly-doped p-type region (120), wherein the oxygen-sensing layer (124) is supported by the 2-dimension hole gas conductive channel (128) and electrically coupled between the ohmic source contact (122) and the ohmic drain contact (126).

Example 4 includes the oxygen sensor of any of examples 1-2, the gateless FET (100) further including a polycrystalline diamond substrate (114), wherein the monocrystalline diamond layer (116) is grown on a first side of the polycrystalline diamond substrate (114).

Example 5 includes the oxygen sensor of any of examples 1-2, the gateless FET (100) further including an ohmic contact substrate (112) supported by a second side of the polycrystalline diamond substrate (114).

Example 6 includes the oxygen sensor of any of examples 1-2, wherein the first highly-doped p-type region (118) is implanted within the monocrystalline diamond layer (116) using boron implantation, and the second highly-doped p-type region (120) is implanted within the monocrystalline diamond layer (116) using boron implantation.

Example 7 includes the oxygen sensor of any of examples 1-2, wherein the 2-dimension hole gas conductive channel (128) formed within the monocrystalline diamond layer (116) by performing hydrogen passivation.

Example 8 includes the oxygen sensor of any of examples 1-3, wherein the ohmic source contact (122) and the ohmic drain contact (126) are formed using a stack of Ti/Au.

Example 9 includes a method of forming a gateless FET oxygen sensor, comprising forming a gateless field effect transistor (FET) (100), and forming an oxygen-sensing layer (124) including a yttrium-stabilized zirconia (YSZ) supported by the gateless FET (100).

Example 10 includes the oxygen sensor of example 9, wherein forming the gateless FET (100) includes growing a synthetic, quasi-intrinsic, hydrogen-passivated, monocrystalline diamond layer (116) on a first side of a polycrystalline diamond substrate (114), generating a first highly-doped p-type region (118) within the mono crystalline diamond layer (116), generating a second highly-doped p-type region (120) within the monocrystalline diamond layer (116), and generating a 2-dimension hole gas conductive channel (128) within the monocrystalline diamond layer (116) between the first highly-doped p-type region (118) and the second highly-doped p-type region (120).

Example 11 includes the oxygen sensor of any of examples 9-10, wherein forming the gateless FET (100) further includes disposing an ohmic source contact (122) on the first highly-doped p-type region (118), and disposing an ohmic drain contact (126) on the second highly-doped p-type region (120).

Example 12 includes the oxygen sensor of any of examples 9-10, wherein forming the gateless FET (100) further includes disposing an ohmic contact substrate (112) on a second side of the polycrystalline diamond substrate (114).

Example 13 includes the oxygen sensor of any of examples 9-10, wherein the first highly-doped p-type region (118) and the second highly-doped p-type region (120) are generated within the monocrystalline diamond layer (116) using boron implantation.

Example 14 includes the oxygen sensor of any of examples 9-10, wherein the 2-dimension hole gas conductive channel (128) occurs within the monocrystalline diamond layer (116) by performing hydrogen passivation.

Example 15 includes the oxygen sensor of any of examples 9-11, wherein the ohmic source contact (122) and the ohmic drain contact (126) are formed using a stack of Ti/Au.

The above Detailed Description is intended to be illustrative, and not restrictive. For example, the above-described examples or one or more elements thereof may be used in combination with each other. Other embodiments may be used, such as by one of ordinary skill in the art upon reviewing the above description. In addition, various features or elements may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the phrase "varus/valgus angle" is used to refer to a varus angle only, a valgus angle only, or both a varus angle and a valgus angle.

In the appended claims, the terms "including" and "in which" are used as the plain-English equivalents of the respective terms "comprising" and "wherein." The terms "including" and "comprising" are open-ended, that is, a system or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

All publications, including non-patent literature (e.g., scientific journal articles), patent application publications, and patents mentioned in this specification are incorporated by reference as if each were specifically and individually indicated to be incorporated by reference.

The Abstract is provided to allow the reader to ascertain the nature of the technical disclosure quickly. It is submitted with the understanding that it will not be used to interpret or limit the scope or meaning of the claims.

What is claimed is:

1. An oxygen sensor, comprising:
    a gateless field effect transistor (FET) (100) including a synthetic, quasi-intrinsic, hydrogen-passivated diamond layer (116) exhibiting a 2-dimension hole gas effect; and
    an oxygen-sensing layer (124) including a yttrium-stabilized zirconia (YSZ) supported by the gateless FET (100).

2. The oxygen sensor of claim 1, the gateless FET (100) further including:
    a first highly-doped p-type region (118) implanted within the monocrystalline diamond layer (116);
    a second highly-doped p-type region (120) implanted within the monocrystalline diamond layer (116); and
    a 2-dimension hole gas conductive channel (128) within the monocrystalline diamond layer (116) between the first highly-doped p-type region (118) and the second highly-doped p-type region (120).

3. The oxygen sensor of claim 2, the gateless FET (100) further including:
an ohmic source contact (122) electrically coupled to the first highly-doped p-type region (118); and
an ohmic drain contact (126) electrically coupled to the second highly-doped p-type region (120);
wherein the oxygen-sensing layer (124) is supported by the 2-dimension hole gas conductive channel (128) and electrically coupled between the ohmic source contact (122) and the ohmic drain contact (126).

4. The oxygen sensor of claim 2, the gateless FET (100) further including a polycrystalline diamond substrate (114), wherein the monocrystalline diamond layer (116) is grown on a first side of the polycrystalline diamond substrate (114).

5. The oxygen sensor of claim 2, the gateless FET (100) further including an ohmic contact substrate (112) supported by a second side of the polycrystalline diamond substrate (114).

6. The oxygen sensor of claim 2, wherein:
the first highly-doped p-type region (118) is implanted within the monocrystalline diamond layer (116) using boron implantation; and
the second highly-doped p-type region (120) is implanted within the monocrystalline diamond layer (116) using boron implantation.

7. The oxygen sensor of claim 2, wherein:
the 2-dimension hole gas conductive channel (128) is formed within the monocrystalline diamond layer (116) by performing hydrogen passivation.

8. The oxygen sensor of claim 3, wherein the ohmic source contact (122) and the ohmic drain contact (126) are formed using a stack of Ti/Au.

9. A method of forming a gateless FET oxygen sensor, comprising:
forming a gateless field effect transistor (FET) (100); and
forming an oxygen-sensing layer (124) including a yttrium-stabilized zirconia (YSZ) supported by the gateless FET (100).

10. The oxygen sensor of claim 9, wherein forming the gateless FET (100) includes:
growing a synthetic, quasi-intrinsic, hydrogen-passivated diamond layer (116) on a first side of a polycrystalline diamond substrate (114);
generating a first highly-doped p-type region (118) within the monocrystalline diamond layer (116);
generating a second highly-doped p-type region (120) within the monocrystalline diamond layer (116); and
generating a 2-dimension hole gas conductive channel (128) within the monocrystalline diamond layer (116) between the first highly-doped p-type region (118) and the second highly-doped p-type region (120).

11. The oxygen sensor of claim 10, wherein forming the gateless FET (100) further includes:
disposing an ohmic source contact (122) on the first highly-doped p-type region (118); and
disposing an ohmic drain contact (126) on the second highly-doped p-type region (120).

12. The oxygen sensor of claim 10, wherein forming the gateless FET (100) further includes disposing an ohmic contact substrate (112) on a second side of the polycrystalline diamond substrate (114).

13. The oxygen sensor of claim 10, wherein the first highly-doped p-type region (118) and the second highly-doped p-type region (120) are generated within the monocrystalline diamond layer (116) using boron implantation.

14. The oxygen sensor of claim 10, wherein the 2-dimension hole gas conductive channel (128) is generated within the monocrystalline diamond layer (116) by performing hydrogen passivation.

15. The oxygen sensor of claim 11, wherein the ohmic source contact (122) and the ohmic drain contact (126) are formed using a stack of Ti/Au.

\* \* \* \* \*